United States Patent [19]

Herzog et al.

[11] Patent Number: 5,001,232

[45] Date of Patent: Mar. 19, 1991

[54] CARBOXYMETHYLSULPHOETHYL CELLULOSES AND A PROCESS FOR THEIR PREPARATION

[75] Inventors: Dieter Herzog; Klaus Balser; Klaus Szablikowski, all of Walsrode, Fed. Rep. of Germany

[73] Assignee: Wolff Walsrode AG, Walsrode, Fed. Rep. of Germany

[21] Appl. No.: 282,077

[22] Filed: Dec. 9, 1988

[30] Foreign Application Priority Data

Dec. 11, 1987 [DE] Fed. Rep. of Germany ....... 3742106

[51] Int. Cl.$^5$ ................... C08B 11/193; C08B 11/00; C08B 11/12
[52] U.S. Cl. ........................................ 536/90; 536/92; 536/98
[58] Field of Search .............................. 536/90, 92, 98

[56] References Cited

U.S. PATENT DOCUMENTS 2,811,519 10/1957 Touey ..................................... 536/92
4,650,863 3/1987 Felcht et al. ........................... 536/90

FOREIGN PATENT DOCUMENTS 63-182301 7/1988 Japan ..................................... 536/91
794098 1/1981 U.S.S.R. .

*Primary Examiner*—Nathan M. Nutter
*Attorney, Agent, or Firm*—Sprung Horn Kramer & Woods

[57] ABSTRACT

Improved water soluble carboxymethylsulphoethyl celluloses may be obtained by suspending cellulose, adding compounds which transfer sulphoalkyl and carboxymethyl and then etherifying after alkalization.

20 Claims, No Drawings

CARBOXYMETHYLSULPHOETHYL CELLULOSES AND A PROCESS FOR THEIR PREPARATION

This invention relates to carboxymethylsulphoethyl celluloses, to a process for their preparation and to compounds obtainable by this process.

Carboxymethylsulphoethyl cellulose (hereinafter CMSEC) is a water soluble, ionic cellulose ether. CMSEC is much less sensitive to the addition of polyvalent ions or different pH-values than the industrially most important cellulose ether, carboxymethyl cellulose (CMC).

Another important criterion for the use of cellulose ethers is the high quality of solution required. The quality of the solution is deleteriously affected by gel particles and by fibres. These gel particles and fibres are due to cellulose particles which have not been completely etherified. They can be determined quantitatively by measuring the transmission of the aqueous solution of the cellulose ether.

Sulphoethyl cellulose has been disclosed e.g. in U.S. Pat. No. 2,811,519 and its use in drilling fluids in U.S. Pat. No. 4,519,923.

CMSEC is known, for example, from U.S. Pat. No. 2,811,519. The use of CMSEC as viscosifier for textile printing inks is described in SU 79 40 98 which claims the use of CMSEC with a $DS_{carboxymethyl}$ of 0.4 to 0 55 and a $DS_{sulphoethyl}$ of 0 1 to 0.25 as viscosity increasing agent in textile printing inks. The term "$DS_{carboxymethyl}$" is used in the present context to denote the average substitution of a glucose unit of cellulose with a carboxymethyl group. The term "$DS_{sulphoethyl}$" is used to denote the average substitution of a glucose unit of cellulose with sulphoethyl groups. The quality of solution of the CMSEC described in the above publication is, however, poor. This CMSEC is said to have a transmission of 89.5% in a 0.5% aqueous solution.

It was an object of the present invention to find a CMSEC which would have a better solution quality over a wide viscosity range and within a wide range of variation of the degree of substitution of carboxymethyl and of the degree of substitution of sulphoethyl.

The present invention relates to a carboxymethylsulphoethyl cellulose (CMSEC) having 1. a degree of substitution $DS_{sulphoethyl}$ of from 0.1 to 1 and a degree of substitution $DS_{carboxymethyl}$ of from 0.3 to 1.2, the degrees of substitution satisfying the following equation:

$$0.5 \leq DS_{sulphoethyl} + DS_{carboxymethyl} \leq 1.6,$$

2. a viscosity as measured on a 2% by weight solution of 5 mPa.s to 60,000 mPa.s (determined at a shear rate of 2.5 s$^{-1}$ and 20° C.) and
3. a transmission as a 2% by weight aqueous solution of T>95% (wavelength used: λ=550 nm, optical path length of the cell=10 mm).

In a particularly preferred embodiment, the degree of substitution $DS_{sulphoethyl}$ is 0.3 to 1.0 and the degree of substitution $DS_{carboxymethyl}$ is 0.3 to 1.2.

The invention further relates to a process for the preparation of a CMSEC by the etherification of cellulose in an alkaline solution with at least one compound SA which transfers a sulphoalkyl group and at least one compound CM transferring a carboxymethyl group, characterised in that (a) cellulose, for example in the form of a finely ground pulp, is suspended, in particular in a secondary or tertiary alcohol,
(b) the suspension is combined with compound SA and/or CM, preferably to result in a pH of 0 to 9,
(c) the suspension is made alkaline, preferably to a pH of 13 to 14, in particular by the addition of an alkali,
(d) etherification is carried out, in particular at a temperature from 55° to 100° C., and
(e) compound CM and/or SA is then added if indicated, in particular at temperatures from 15° to 100° C. and at a pH of 10 to 14, to form a CMSEC.

In a particularly preferred embodiment of the process, only SA is added at reaction step (b) and only CM is added at reaction step (e). In another preferred embodiment, only CM is added at reaction step (b) and only SA is added as active substance in reaction step (e).

The invention further relates to carboxymethylsulphoethyl celluloses CMSEC having 1. a degree of substitution $DS_{sulphoethyl}$ of 0.1 to 1 and a degree of substitution $DS_{carboxymethyl}$ of 0.3 to 1.2, the degrees of substitution satisfying the following equation:

$$0.5 \leq DS_{sulphoethyl} + DS_{carboxymethyl} \leq 1.6$$

2. a viscosity as measured on a 2% by weight solution of 5 mPa.s to 60,000 mPa.s (determined at a shear rate of 2.5 s$^{-1}$ and 20° C.) and
3. a transmission in a 2% by weight aqueous solution of T>95% (wavelength used: λ=550 nm, optical path length of the cell=10 mm)

obtainable by the process according to the invention.

The following are preferred sulphoalkyl-transferring compounds SA: chloroethane sulphonic acid, bromoethane sulphonic acid, vinyl sulphonic acid and their salts, particularly the salts of vinyl sulphonic acid, especially the sodium salts.

Chloro-acetic acid, bromo-acetic acid and their salts, in particular chloro-acetic acid, are particularly preferred carboxymethyl-transferring compounds CM. One particularly preferred embodiment uses purified carboxymethyl cellulose prepared according to the state of the art as starting substance of a CMSEC obtained by further etherification. In this process according to the invention, addition of the aqueous solution of sodium vinyl sulphonate used as alkylating agent is carried out before alkalization of the carboxymethyl cellulose. This alkalization of carboxymethyl cellulose can be carried out under milder conditions than in processes using cellulose, i.e. smaller quantities of alkali metal hydroxides may be used and the alkalizing time may be reduced. A certain minimum quantity of alkali metal hydroxides is nevertheless always necessary since catalytic quantities are required for the alkylation with sodium vinyl sulphonate.

It is surprisingly found that a product with good solution qualities is obtained if the addition of an aqueous solution of the sodium vinyl sulphonate used as alkylating agent to a cellulose suspended in a secondary or tertiary alcohol is carried out before the alkalization. Under these conditions, good chemical yields, based on the sodium vinyl sulphonate, are obtained. Ground cellulose powder (chemical conversion pulp) obtained e.g. from cotton linters, purified pine sulphite cellulose or purified pine sulphate cellulose is suspended in a secondary or tertiary alcohol, preferably isopropanol or tert. butanol. The products are adjusted to the desired final viscosity by the exclusion or addition of oxidising substances such as air, $H_2O_2$ or metal oxides and by the choice of the cellulose materials used in the process. This adjustment of the final viscosity is state of the art and well known to the man of the art. Cf. the chapter entitled "Celluloseether" in Ullmann's Encyklopadie der technischen Chemie, volume 9, pages 192 to 212 (Verlag Chemie, Weinheim, 1975).

In the process according to the invention, the products according to the invention are prepared by the addition of an aqueous solution of the alkylating agent, in particular sodium vinyl sulphonate, to the suspension of cellulose before alkalization is carried out, and the mixture is generally stirred for 5 to 60 minutes, preferably 10 to 30 minutes before alk li ation is carried out. This ensures particularly uniform distribution of the alkylating agent on the cellulose.

The addition of alkali metal hydroxides and possibly a further quantity of water converts the cellulose into activated alkali cellulose. After an alkalization time of 60 to 180 minutes at 0° to 35° C., alkylation is generally carried out by increasing the temperature to values from 55° to 100° C., preferably 60° to 80° C. Alkylation is generally carried out within a period of 30 to 300 minutes, preferably 45 to 180 minutes. This is followed by the addition of chloro-acetic acid, e.g. in a crystalline form or as an 80% aqueous solution, and etherification is continued at a temperature from 55° to 100° C., preferably at 55° to 80° C. The chloro-acetic acid may be added at the existing reaction temperature or after cooling of the reaction mixture to temperatures of 15° to 35° C.

Etherification in the second stage may continue for 30 to 600 minutes, preferably from 45 to 210 minutes. If necessary, the reaction mixture is neutralized by the addition of acids (e.g. formic acid, acetic acid, hydrochloric acid). This is always carried out if the quantity of chloro-acetic acid used has not been sufficient to neutralize all the alkali metal hydroxides by their reaction with chloro-acetic acid.

The product obtained is generally separated from the slurry medium (by centrifuging or filtration) and freed from salts adhering thereto by washing with alcohols or alcohol/water mixtures (preferably methanol or methanol/water mixtures).

The products obtained according to the invention are suitable as thickeners or agents for retaining water in the petroleum industry and the manufacture of building materials and as thickeners or stabilizers of detergents and cosmetics. CMSEC is also suitable as dispersing or suspending agent and as auxiliary agent and viscosity forming agent in aqueous systems, e.g. as stabilizer and dispersing and suspending agent for emulsion and suspension polymerisations. The products may also be used as thickeners and stabilizers in systems containing surface active agents, such as cleaning agents and cosmetics.

The parts given in the following examples and tables are parts by weight.

Viscosity measurements were carried out in a rotational viscosimeter of Haake, model RV 100, System M 500, measuring device MV according to DIN 53 019 at a shear rate of $D = 2.5 \text{ sec}^{-1}$ and at a temperature of 20° C. The viscosities were measured on 2% by weight solutions in distilled water.

Transmission measurements were carried out in a Hitachi Spectral Photometer, Modell 101, Hitachi Ltd., Tokyo, Japan. A glass cell having an optical pathlength of 10 mm was used. The wave length used was 550 nm.

EXAMPLE 1

127.4 parts of finely ground (0.02 to 0.5 mm) bleached, refined pine sulphite cellulose are suspended in 2178 parts of isopropanol under atmospheric oxygen in a thermostatically controlled reactor with suitable stirrer. 159 34 parts of a 51.3% vinyl sulphonic acid sodium salt solution in water are added and the reaction mixture is stirred for 15 minutes. 75.46 parts of sodium hydroxide dissolved in 147.4 parts of water are then added and alkalization is carried out for 80 minutes at 25° to 30° C. The reaction mixture is then heated to 70° C. over a period of 60 minutes and the temperature is maintained at 70° C. for 120 minutes. 92.34 parts of an 80% by weight solution of chloro-acetic acid in water are added and the temperature is maintained at 70° C. for a further 90 minutes. The product is then filtered and washed five times, each time with 2000 parts of a mixture of 3 parts of water and 7 parts of methanol, and finally once with 2000 parts of pure methanol. The product is dried in air.

EXAMPLES 2 TO 6

The method of preparation is analogous to that of Example 1 but the whole reaction is carrIed out under an atmosphere of nitrogen. The exact production data are shown in Table 1.

EXAMPLE 7

127.33 parts of purified pine sulphite cellulose are suspended in 2178 parts of isopropanol under a nitrogen atmosphere in a thermostatically controlled closed reaction vessel equipped with a suitable stirrer. 75.46 parts of sodium hydroxide dissolved in 225 parts of water are added. The resulting mixture is stirred at 25° to 30° C. The cellulose is converted into activated alkali cellulose. 80.44 g of an 80% by weight solution of chloro-acetic acid in water are then added and the reaction mixture is heated to 70° C. in 30 minutes. This temperature is maintained for 90 minutes. 50 g of glacial acetic acid are then added to neutralize the excess sodium hydroxide solution. The product is filtered off and repeatedly washed with 70% methanol until no more sodium chloride can be detected in the washing liquid. The product is dried in air. After drying, it has a residual moisture content of 16.22% of water and a degree of substitution DS carboxymethyl of 0.47.

119.12 parts of this product are suspended in 2237 parts of isopropanol under a nitrogen atmosphere in a reaction vessel as described above. 42.9 parts of a 30.3% by weight solution of sodium vinyl sulphonate are added and the reaction mixture is stirred for 15 minutes. 20 parts of sodium hydroxide dissolved in 120 parts of water are added and alkalization is carried out for 60 minutes at 25° to 30° C. The reaction mixture is then heated to 70° C. within 60 minutes and this temperature is maintained for 150 minutes. 30 parts of acetic acid are added to neutralize the reaction mixture. The product is filtered off and washed five times, each time with 2000 parts of a mixture of 7 parts of methanol and 3 parts of water. The product is then dried in air.

EXAMPLE 8

The method of reaction is analogous to that of Example 7 but the quantity of vinyl sulphonic acid sodium salt used is 85.81 parts of a 30.3% solution. After the addition of the solution of vinyl sulphonic acid sodium salt, 20 parts of sodium hydroxide are dissolved in 90.2 parts of water and added after 15 minutes.

The data of the products according to the invention are summarized in Table 2.

TABLE 1

Conditions of preparation

EXAMPLES 1 TO 6

Legend to Table 2.

| VSSNa: | sodium vinyl sulphonate |
|---|---|
| NaOH: | sodium hydroxide |
| H₂O: | water |
| 80% by weight CES solution: | chloro-acetic acid solution, 80% by weight |
| Reaction time I: | reaction time for alkylation with sodium vinyl sulphonate |
| Reaction time II: | reaction time for alkylation with chloro-acetic acid after the addition of 80% chloro acetic acid solution |
| Linters: | chemical conversion pulp obtained from ground, bleached cotton linters, particle size < 0.4 mm |
| Pine: | chemical conversion pulp from ground, bleached pine cellulose, particle size < 0.4 mm |
| N₂: | the whole reaction was carried out under a nitrogen atmosphere |
| Air: | the whole reaction was carried out under an atmosphere of air. |

TABLE 2

Product data

EXAMPLES 1 TO 8

Legends to Table 3.

| Dry content: | crude product (air dried) minus moisture, given in % |
|---|---|
| DS: | degree of substitution, number of substituents per anhydroglycose unit |
| Chemical yield: | quantity of alkylating agent reacted to the product in % of the sodium vinyl sulphonate used. |
| Transmission: | proportion of light which penetrates in % of the incident light on passage through a cell filled with a 2% cellulose ether solution. Optical pathlength of the cell = 10 mm, wavelength used $\lambda$ = 550 nm. |

TABLE 1

| | | | | | | Conc. of | |
| | | | | Type of | VSSNa | VSSNa | |
| Example | iPrOH | MeOH | Cellulose | Cell- | solution | solution | NaOH |
| No. | (parts) | (parts) | (parts) | lose | (parts) | (% by weight) | (parts) |
|---|---|---|---|---|---|---|---|
| 1 | 2.178 | — | 127.41 | Pine | 79.67 | 51.3 | 75.46 |
| 2 | 2.178 | — | 127.41 | Pine | 278.85 | 51.3 | 75.46 |
| 3 | 2.178 | — | 127.41 | Linters | 159.34 | 51.3 | 75.46 |
| 4 | 2.178 | — | 127.41 | Linters | 278.85 | 51.3 | 75.46 |
| 5 | 2.178 | — | 127.41 | Linters | 159.34 | 51.3 | 75.46 |
| 6 | 2.178 | — | 127.41 | Linters | 79.67 | 51.3 | 75.46 |

| | | 80% by weight | Heating | Reaction | Reaction | | |
| | | CES | up | time | time | Reaction | |
| Example | H₂O | solution | time | I | II | temperature | |
| No. | (parts) | (parts) | (min) | (min) | (min) | (°C.) | atmosphere |
|---|---|---|---|---|---|---|---|
| 1 | 186.2 | 110.81 | 60 | 120 | 90 | 70 | air |
| 2 | 135.8 | 92.34 | 60 | 120 | 90 | 70 | air |
| 3 | 147.4 | 110.81 | 60 | 120 | 90 | 70 | air |
| 4 | 89.2 | 92.34 | 60 | 120 | 90 | 70 | N2 |
| 5 | 147.4 | 110.81 | 60 | 120 | 90 | 70 | N2 |
| 6 | 186.2 | 110.81 | 60 | 120 | 90 | 70 | N2 |

TABLE 2

| | | | Product Data | | | |
| Example Number | Dry Content (%) | Viscosity 2% in dis. H₂O (mPa.s) | DS Sulphoethyl | DS Carboxymethyl (%) | Trans- missivity (%) | Chemical yield (%) |
|---|---|---|---|---|---|---|
| 1 | 83.3 | 59 | 0.53 | 0.74 | 97.8 | 66.25 |
| 2 | 80.3 | 127 | 0.8 | 0.48 | 97.7 | 57.14 |
| 3 | 84.11 | 39.058 | 0.24 | 0.72 | 95.9 | 60 |
| 4 | 85.29 | 40.850 | 0.1 | 0.8 | 95.1 | 50 |
| 5 | 85.62 | 38.342 | 0.32 | 0.59 | 96.5 | 53.33 |
| 6 | 85.36 | 31.677 | 0.34 | 0.74 | 96.6 | 56.66 |
| 7 | 83.9 | 309 | 0.12 | 0.47 | 97 | 60 |
| 8 | 81.1 | 178 | 0.21 | 0.47 | 96 | 52.5 |

EXAMPLE 9

Table 3 shows the viscosities of a series of products according to the invention compared with a commercial carboxymethyl cellulose in a mixed salt system. The products according to the invention are seen to have a markedly higher viscosity in the mixed salt system than carboxymethyl cellulose. For better comparability, the viscosity in the mixed salt system was referred to the viscosity in distilled water. It is given in % of the viscosity measured in distilled water.

TABLE 3

| | Viscosities in Mixed Salt Systems. | | |
|---|---|---|---|
| Example | Viscosity dist. water (mPa.s) | Factor Mixed Salt System Room Temperature (%) | Factor Mixed Salt System 80° C. (%) |
| 1 | 104.5 | 103.8 | 98.1 |
| 2 | 99.0 | 104.0 | 97.0 |
| 3 | 92.0 | 102.2 | 96.2 |
| 4 | 94.5 | 105.8 | 98.4 |
| CMC | 104.0 | 95.2 | 89.9 |

Legend to Table 3:

The viscosities were determined on 1% by weight solutions, using a rotational viscosimeter of the type Baroid Variable Speed Rheometer No. 286. The measurements were taken according to the standards of the American Petroleum Institute (API, RP 13 B, 6th Edition, April 1986, issued by American Petroleum Institute, Production Department, 300 Carreegan Tower Building, Dallas, Tex. 75201, USA). The measurements shown in column 3 were carried out after 16 hours storage at room temperature. The measurements in column 4 were obtained after 24 hours storage at room temperature followed by 16 hours storage at 80° C. The viscosity measurements were carried out at 25° C. and a shear gradient of 1.021 sec$^{-1}$.

The relative viscosity in the mixed salt system (given in %) in columns 3 and 4 is based on the viscosity of the same product in distilled water, as follows:

Factor mixed salt system =

$$\frac{\text{viscosity in mixed salt system (mPa} \cdot \text{s)}}{\text{viscosity in distilled H}_2\text{O (mPa} \cdot \text{s)}} \times 100\%$$

Composition of the mixed salt system:

| |
|---|
| 60 g NaCl |
| +20 g CaCl$_2$ · 2 H$_2$O |
| +20 g MgCl$_2$ · 6 H$_2$O |
| +1000 g water |

The carboxymethyl cellulose used for comparison is a commercial carboxymethyl cellulose with a degree of substitution of DS=0.9 as used for deep well drilling.

We claim:

1. Carboxymethylsulphoethyl cellulose (CMSEC) having
   1. a degree of substitution $DS_{sulphoethyl}$ of 0.1 to 1 and a degree of substitution $DS_{carboxymethyl}$ of 0.3 to 1.2, the degrees of substitution satisfying the following equation:

$$0.5 \leq DS_{sulphoethyl} + DS_{carboxymethyl} \leq 1.6,$$

2. a viscosity as measured on a 2% by weight solution of 5 mPa.s to 60,000 mPa.s (determined at a shear rate $\gamma$ of 2.5 s$^{-1}$ and 20° C.) and
   3. a transmission in 2% by weight aqueous solution of T>95% (wave length of the light used: $\lambda=550$ nm, optical path length of cell=10 mm).

2. Carboxymethylsulphoethyl cellulose according to claim 1, wherein the degree of substitution $DS_{sulphoethyl}$ is 0.3 to 1.0 and the degree of substitution $DS_{carboxymethyl}$ is 0.3 to 1.2.

3. Process for the preparation of a carboxymethylsulphoethyl cellulose by etherification of cellulose in alkaline solution with at least one compound SA which transfers a sulpho alkyl group and at least one compound CM which transfers a carboxymethyl group, wherein
   (a) cellulose is suspended,
   (b) the suspension is combined with compound SA and/ or CM,
   (c) the reaction mixture is then made alkaline,
   (d) etherification is carried out,
   (e) compound CM and/or SA is then added, 4. Process for the preparation of a carboxymethylsulphoethyl cellulose according to claim 3, wherein in reaction step (b) only compound SA is added and in reaction step (e) only compound CM is added.

5. Process according to claim 3, wherein in reaction step (b) only CM is added and in reaction step (e) only SA is added.

6. Process for the preparation of a carboxymethylsulphoethyl cellulose CMSEC by the etherIfication of carboxymethyl cellulose CMC in alkaline solution with at least one compound SA which transfers a sulpho alkyl group, wherein
   (a) CMC is suspended,
   (b) the suspension is combined with compound SA,
   (c) the reaction mixture is made alkaline, and
   (d) etherification is carried out, with the formation of a CMSEC.

7. Carboxymethylsulphoethyl cellulose having
   1. a degree of substitution $DS_{sulphoethyl}$ of 0.1 to 1 and a degree of substitution $DS_{carboxymethyl}$ of 0.3 to 1.2, the degrees of substitution satisfying the following equation:

$$0.5 \leq DS_{sulphoethyl} + DS_{carboxymethyl} \leq 1.6,$$

2. a viscosity as measured on a 2% by weight solution of 5 mPa.s to 60,000 mPa.s (determined at a shear rate of 2.5 s$^{-1}$ and 20° C.) and
   3. a transmission in a 2% by weight aqueous solution of T>95% (wave length of the light used: $\lambda=550$ nm, optical pathlength of cell=10 mm), obtainable according to the process of claim 3 or 6.

8. A process according to claim 3 wherein in (a) the cellulose is in the form of a pulp.

9. A process according to claim 3 wherein in (a) the cellulose is suspended in a secondary or tertiary alcohol.

10. A process according to claim 3 wherein in (b) the combination of the suspension and SA and/or CM results in a pH of 0 to 9.

11. A process according to claim 3 wherein in (c) the reaction mixture is made alkaline to pH 13 to 14.

12. A process according to claim 11 wherein the reaction mixture is made alkaline to pH 13 to 14 by the addition of alkali.

13. A process according to claim 3 wherein in (d) the etherification is carried out at a temperature of 55° to 100° C.

14. A process according to claim 3 wherein in (e) the compound CM and/or SA is added at temperatures from 15° to 100° C. and at a pH 10 to 14.

15. A process according to claim 6 wherein in (a) CMC is suspended in a secondary or tertiary alcohol.

16. A process according to claim 6 wherein in (b) the suspension is combined with compound SA to result in a pH of 0 to 9.

17. A process according to claim 6 wherein in (c) the reaction mixture is made alkaline to a pH 13 to 14.

18. A process according to claim 17 wherein the reaction mixture is made alkaline to a pH 13 to 14 by the addition of alkali.

19. A process according to claim 6 wherein in (d) the etherification is carried out at a temperature of from 55° to 100° C.

20. Carboxymethylsulphoethyl cellulose having
1. a degree of substitution $DS_{sulphoethyl}$ of 0.1 to 1 and a degree of substitution $DS_{carboxymethyl}$ of 0.3 to 1.2, the degrees of substitution satisfying the following equation:

$$0.5 \leq DS_{sulphoethyl} + DS_{carboxymethyl} \leq 1.6.$$

2. a viscosity as measured on a 2% by weight solution of 5 mPa.s to 60,000 mPa.s (determined at a shear rate of 2.5 s$^{-1}$ and 20° C.) and
3. a transmission in a 2% by weight aqueous solution of T>95% (wave length of the light used:=550 nm, optical pathlength of cell=10 mm), obtainable according to the process of claim 6.

* * * * *

UNITED STATES PATENT AND TRADEMARK OFFICE
CERTIFICATE OF CORRECTION

PATENT NO. : 5,001,232

DATED : March 19, 1991

INVENTOR(S) : Herzog et al.

It is certified that error appears in the above-identified patent and that said Letters Patent is hereby corrected as shown below:

Col. 8, line 9   After " added " insert -- with the formation of a CMSEC.--

Col. 8, line 42  Delete " or 6 "

Signed and Sealed this

Twenty-fifth Day of May, 1993

Attest:

MICHAEL K. KIRK

Attesting Officer

Acting Commissioner of Patents and Trademarks